United States Patent [19]

Buxton et al.

[11] Patent Number: 5,112,515
[45] Date of Patent: May 12, 1992

[54] PHENOTHRIN SHAMPOO

[75] Inventors: Ian R. Buxton; Sandra T. A. Malkowska; Derek A. Prater; Deborah L. Singh; Stewart T. Leslie, all of Cambridge, United Kingdom; Ronald B. Miller, Basel, Switzerland

[73] Assignee: Euroceltique, S.A., Luxembourg

[21] Appl. No.: 650,677

[22] Filed: Feb. 5, 1991

[30] Foreign Application Priority Data

Feb. 9, 1990 [GB] United Kingdom ............... 9003017

[51] Int. Cl.⁵ ............... C11D 3/48; A61K 7/06
[52] U.S. Cl. ............... 252/106; 252/DIG. 13; 424/70
[58] Field of Search ............ 252/106, DIG. 13; 424/70

[56] References Cited

U.S. PATENT DOCUMENTS 4,336,270  6/1982  Muntwyler .................. 424/347

FOREIGN PATENT DOCUMENTS 174347   10/1983  Japan.
270516   11/1987  Japan.
2204243  11/1988  United Kingdom.
2222949   3/1990  United Kingdom.
9000859   2/1990  World Int. Prop. O.

OTHER PUBLICATIONS

*The Pesticide Manual*, The Edition, pp. 68 and 431 (The British Crop Protection Council).
*Chemical Abstracts* 103(22):183364.
*McCutcheon's Functional Materials*, McPublishing Co., 1977, pp. 11 and 16.

Primary Examiner—A. Lionel Clingman
Assistant Examiner—Mary C. DiNunzio
Attorney, Agent, or Firm—Steinberg & Raskin

[57] ABSTRACT

The invention relates to a lousicidal shampoo composition of phenothrin as lousicidal agent distributed in a shampoo base of water and one or more surface active agents, the shampoo containing as antimicrobial preservative 2-bromo-2-nitropropane-1,3-diol alone or in combination with 2,4-dichlorobenzyl alcohol.

13 Claims, No Drawings

PHENOTHRIN SHAMPOO

BACKGROUND OF THE INVENTION

It is desirable to provide lousicidal compositions. An ideal lousicidal composition should meet at least the following requirements, namely:

(i) the composition should be convenient and easy to use;
(ii) the composition should be capable of "one-shot" use, that is one application of the composition should be capable of dealing with a case of louse infestation;
(iii) the composition should be stable and have an acceptable shelf-life.

SUMMARY OF THE INVENTION

The invention relates to improvements in lousicidal compositions, particularly to compositions for topical application to the scalp and hair for the purpose of killing arthropod parasites such as lice and/or their ova (ova). The invention is particularly directed to shampoo compositions which contain phenothrin as lousicidal agent.

It is accordingly a primary object of the present invention to provide a shampoo composition which contains phenothrin as lousicidal agent and which provides all of the above desired properties for such lousicidal shampoo composition.

It is another object of the present invention to provide a phenothrin shampoo which can be easily and readily applied to the hair and scalp and which is susceptible of one shot application for the treatment of lice.

Other objects and advantages of the present invention will be apparent from a further reading of the specification and of the appended claims.

With the above and other objects in view, the present invention comprises a lousicidal composition which is a shampoo containing phenothrin as lousicidal agent, together with a shampoo base of water and at least one surface active agent, the shampoo composition containing as antimicrobial preservative 2-bromo-2-nitropropane-1,3-diol, either alone or in combination with 2,4-dichlorobenzyl alcohol.

The present invention further provides a method for controlling lice or their ova which comprises topical application of a lousicidal shampoo comprising a lousicidally effective amount of phenothrin and an antimicrobial preservative which is either 2-bromo-2-nitropropane-1-3-diol alone or in combination with 2,4-dichlorobenzyl alcohol, the phenothrin and the antimicrobial agent being distributed in a shampoo base of water and at least one surface active agent.

The amount of phenothrin in the shampoo composition of the present invention should be sufficient to control lice or their ova and the amount which is suitable for the purposes of the present invention is between about 0.05-10% by weight of the shampoo, preferably 0.1-10% by weight and most preferably about 0.2% by weight.

As indicated, the shampoo base comprises water and at least one surface active agent or surfactant, preferably a mixture of surfactants. The water suitably forms about 5-90% by weight of the base, preferably about 20-60% by weight and most preferably about 40% by weight, the balance of the shampoo base comprising mainly the surfactant component. In addition, there may be smaller amounts, up to about 20% by weight of the total, of ingredients such as preservatives, pH adjusters, buffering agents, dyes, foam boosters, viscosity adjusting agents, foam stabilizers, antioxidants, chelating agents, conditioning agents, coloring agents, perfumes, etc.

The surface active components typically comprise one or more pharmaceutically acceptable anionic surface active agents, particularly alkali metal alkyl ether sulfates such as sodium lauryl ether sulfate, generally forming about 10% by weight of the surface active component, together with one or more non-ionic surface active agent such as polyethyleneglycol, polyethoxylated alkyl phenols, polyethoxylated alcohols and long chain fatty acid mono- and di-alkanolamides.

In accordance with the preferred embodiments of the invention, the non-ionic surface active component is such as to dissolve the phenothrin in the base, and is present in the shampoo base in a sufficient quantity to achieve such dissolution, thus increasing its effectiveness. To this end, the shampoo in accordance with the invention suitably contains relatively large amounts of non-ionic surfactants, e.g. 10-50% by weight based on the total weight of the shampoo.

As noted above, the shampoo of the invention will also generally contain other ingredients in minor amounts, for example pH adjusters, buffering agents, coloring agents, and perfumes, provided of course that they are pharmaceutically acceptable, compatible with the lousicide and soluble in water. The nature and amounts of such other ingredients are such as are commonly used in shampoos or so-called "medicated" shampoos.

We have found that, in order to meet the specification prescribed in the British Pharmacopoeia 1988 "Efficacy of Antimicrobial Preservatives in Pharmaceutical Products", many conventional preservatives in conventional amounts do not afford adequate antimicrobial protection. We have found, however, that the preservative (trade name "bronopol"), 2-bromo-2-nitropropane-1,3,-diol, especially when used in conjunction with the preservative 2,4-dichlorobenzyl alcohol (trade name "Myacide"), affords good antimicrobial protection. Surprisingly, there appears to be interdependence between the preservative component and the phenothrin, since the same shampoo composition, in which phenothrin is replaced by another lousicide, carbaryl, does not show adequate antimicrobial properties.

When bronopol is used as preservative alone it is suitably present in the shampoo in an amount of 0.05 to 0.2% by weight; when a combination of bronopol and Myacide SP are employed together as preservatives they are suitably used in amounts of 0.01 to 0.2 and 0.5 to 0.5% by weight, respectively. When bronopol is present as preservative, the composition according to the invention desirably contains an antioxidant such as butylated hydroxytoluene, butylated hydroxyanisole or ascorbic acid to prevent degradation of the preservative, with butylated hydroxytoluene being preferred.

The composition accordingly to the present invention may be used to control lice or their ova by applying the composition to the site of infestation. Alternatively, the composition may be used prophylactically to prevent infestation.

In a further aspect, the invention provides a process for preparing a lousicidal shampoo containing phenothrin as lousicide agent and bronopol either alone or in combination with Myacide as preservative, which comprises distributing a lousicidally effective amount of phenothrin, bronopol and optionally Myacide and one or more surface active agents in water.

DESCRIPTION OF PREFERRED EMBODIMENTS

The following examples are given to further illustrate the present invention. The scope of the invention is not, however, meant to be limited to the specific details thereof.

EXAMPLE 1

A shampoo having the following formulation was prepared;

| | % w/w |
|---|---|
| Phenothrin | 0.2 |
| Bronopol BP | 0.1 |
| Myacide SP | 0.1 |
| Butylated hydroxytoluene | 0.05 |
| Sodium lauryl ether sulphate 70% | 20.0 |
| Polyethylene glycol 400 USNF | 4.0 |
| Coconut diethanolamide (Comperlan KD) | 1.0 |
| Nonoxynol-9 USP | 12.4 |
| Ethoxylated Lanolin 50% | 3.0 |
| Buffering agents, dyes, perfumes as required | |
| Purified Water EP | to 100 |

Purified water equivalent to approximately 50% of the batch weight was placed in a mixer and heated to approximately 80° C. Coconut diethanolamide, sodium lauryl ether sulphate 70%, ethoxylated lanoline 50%, polyethylene glycol 400, nonoxynol-9 and butylated hydroxytoluene were added and mixed to obtain a uniform dispersion. The remaining minor ingredients were added as required and mixed.

The solution was cooled to 60° C. and phenothrin and Myacide added with mixing. The solution was further cooled to 30° C. and a solution of bronopol in purified water added. Further purified water was added to achieve the final batch weight of 500 kg and the whole was again mixed until uniform.

MICROBIOLOGICAL TEST

The test procedure conformed with the specifications described in the 1988 British Pharmacopoeia—"Efficacy of Antimicrobial Preservatives in Pharmaceutical Products".

1. Inoculation of Product

Aliquots of microbial suspensions of *Pseudomonas aeruoinosa* NC18 8626, Stahylococcus aureus NCTC 10788, *Candida albicans* NCPF 3179, and *Asperoillus niger* IMI 149007 were introduced into separate containers of the composition of Example 1 to achieve a final concentration of approximately $1 \times 10^6$ cfu/ml. The same volume of inoculum was simultaneously introduced into separate equivalent quantities of 0.1% peptone water to be used as controls. The inoculated product was stored in the dark at 20°-25° C.

2. Recovery of Microorganisms 1 ml aliquots of the inoculated product were removed at 0, 6, 24 and 48 hours, 7, 14 and 28 days. Each was added to 9 ml of 0.1% peptone water containing the following as preservative inactivating agents:

| | |
|---|---|
| Polysorbate | 1.0% |
| Lecithin | 0.5% |
| Cirrasol | 1.0% |
| Sodium thiosulphate | 1.0% |

The control preparations were similarly sampled at 0 hours to determine the viable counts of the cultures used and to confirm the suitability of the media used for their growth.

Further dilutions were made as necessary in 0.1% peptone water and 1 ml aliquots of all dilutions were incorporated in pour plates of the appropriate cooled molten agar containing 0.1% cysteine hydrochloride.

The pour plates were incubated at 30° C. for three days for the bacteria and at 23° C. for five days for the yeasts and mould.

After incubation the number of colonies on each plate were counted and, taking the dilution factor into account, the number of cfu/ml of product calculated.

These figures are listed in the tables.

3. Validation of Recovery Counts

The suspensions of the test organisms were further diluted with 0.1% peptone water to approximately $10^2$ cfu/ml.

Three petri dishes were used for each organism and 0.1 ml of the relevant suspension added to each plate. To the first set of plates 1 ml of product diluted 10 fold in recovery medium was added, to the second set 1 ml of product diluted 100 fold was added and the third set acted as a control having no product in them. The appropriate cooled molten agar was then added to the plates which were incubated as described above. The plates were then examined for growth and the number of colonies present recorded on the raw data sheet.

| RESULTS Control Count at 0 Hour | |
|---|---|
| Organism | cfu/ml |
| C. albicans | $140 \times 10^4$ |
| A. niger | $80 \times 10^4$ |
| P. aeruginosa | $120 \times 10^4$ |
| S. aureus | $68 \times 10^4$ |
| B 141 | $60 \times 10^4$ |

VALIDATION OF RECOVERY COUNTS

No inhibition was noted on any of the validation plates. Counts of <5 cfu/ml are therefore valid.

RECOVERY COUNTS FOR EXAMPLE 1

Phenothrin Shampoo (0.1% Bronopol+0.1% Myacide).

A topical preparation is considered to be effectively preserved if the following criteria are met:

Bacteria—the number of organisms recovered per ml is reduced by a factor of not less than $10^3$ within 48 hours of challenge and no organism is recovered from 1 ml at 7 days and thereafter;

Moulds and Yeasts—the number of organisms recovered per ml is reduced by a factor of not less than $10^2$ within 14 days of challenge and there is no increase thereafter.

From the results below it can be seen that the shampoo of Example 1 meets these requirements.

| | MEAN COUNTS/ML SAMPLE AFTER | | | | | | |
|---|---|---|---|---|---|---|---|
| | 0 hr | 6 hr | 24 hr | 68 hr | 7 days | 14 days | 28 days |
| C. albicans | 138 × 10⁴ | 74 × 10⁴ | 114 × 10³ | 90 | <5 | <5 | <5 |
| A. niger | 61 × 10⁴ | 68 × 10³ | 34 × 10³ | 140 × 10² | <5 | <5 | <5 |
| P. aeruginosa | 106 × 10⁴ | <5 | <5 | <5 | <5 | <5 | <5 |
| S. aureus | 72 × 10⁴ | 189 × 10² | <5 | <5 | <5 | <5 | <5 |

While the invention has been illustrated with respect to particular compositions, it is apparent that variations and modifications of the invention can be made.

What is claimed is:

1. Lousicidal shampoo composition comprising a shampoo base comprising from about 5 to about 90 percent water and at least one surface active agent, said shampoo base having distributed therethrough a lousicidal effective amount of phenothrin and an antimicrobial preservative effective amount of 2-bromo-2-nitropropane-1,3-diol alone or in combination with 2,4-dichlorobenzyl alcohol, said at least one surface active agent being in an amount effective to dissolve said phenothrin in said shampoo base.

2. Shampoo composition according to claim 1 wherein the amount of phenothrin is about 0.05–10% by weight.

3. Shampoo composition according to claim 1 wherein said phenothrin is present in an amount of about 0.01–1% by weight.

4. Shampoo composition according to claim 1 wherein said antimicrobial preservative is 2-bromo-2-nitropropane-1,3-diol in an about of about 0.05–0.2% by weight.

5. Shampoo composition according to claim 1 wherein said antimicrobial preservative is 0.01–0.2% by weight of 2-bromo-2-nitropropane-1,3-diol and 0.05–0.5% by weight of 2,4-dichlorobenzyl alcohol.

6. Shampoo composition according to claim 2 wherein said antimicrobial preservative is 2-bromo-2-nitropropane-1,3-diol in an amount of about 0.01–0.2% by weight.

7. Shampoo composition according to claim 3 wherein said antimicrobial preservative is 2-bromo-2-nitropropane-1,3-diol in an amount of about 0.05–0.2% by weight.

8. Shampoo composition according to claim 3 wherein said antimicrobial preservative is 0.01–0.2% by weight of 2-bromo-2-nitropropane-1,3-diol and 0.05–0.5% by weight of 2,4-dichlorobenzyl alcohol.

9. Shampoo composition according to claim 1 which further comprises an effective amount of an antioxidant.

10. Shampoo composition according to claim 9 wherein said antioxidant is butylated hydroxytoluene.

11. Composition according to claim 1 wherein said surface active agent comprises a mixture of at least one anionic surface active agent and at least one non-ionic surface active agent.

12. Method of producing the shampoo composition of claim 1 which comprises distributing said phenothrin, said antimicrobial preservative and said surface active agents in water.

13. Method for the control of lice or their ova which comprises applying to the site of infestation of lice or their ova a shampoo composition comprising a lousicidal effective amount of phenothrin, 2-bromo-2-nitropropane-1,3-diol as preservative alone or together with 2,4-dichlorobenzyl alcohol distributed in a shampoo base comprising water and at least one surface active agent.

* * * * *